(12) United States Patent
Dufourcq

(10) Patent No.: US 11,305,175 B2
(45) Date of Patent: Apr. 19, 2022

(54) DEVICE FOR MANAGING EFFORT FOR A GYM HALL

(71) Applicant: Mathieu Dufourcq, Boe (FR)

(72) Inventor: Mathieu Dufourcq, Boe (FR)

( * ) Notice: Subject to any disclaimer, the term of this patent is extended or adjusted under 35 U.S.C. 154(b) by 0 days.

(21) Appl. No.: 16/489,186

(22) PCT Filed: Feb. 22, 2018

(86) PCT No.: PCT/FR2018/050426
§ 371 (c)(1),
(2) Date: Aug. 27, 2019

(87) PCT Pub. No.: WO2018/158525
PCT Pub. Date: Sep. 7, 2018

(65) Prior Publication Data
US 2019/0374844 A1    Dec. 12, 2019

(30) Foreign Application Priority Data

Feb. 28, 2017   (FR) ...................................... 17/51646

(51) Int. Cl.
*G06F 3/048*     (2013.01)
*A63B 71/06*     (2006.01)
(Continued)

(52) U.S. Cl.
CPC ...... *A63B 71/0622* (2013.01); *A63B 24/0062* (2013.01); *G05B 19/042* (2013.01);
(Continued)

(58) Field of Classification Search
CPC ............ A63B 71/0622; A63B 24/0062; G05B 19/042; G06F 3/1423; G06F 3/165; H04H 20/61
See application file for complete search history.

(56) References Cited

U.S. PATENT DOCUMENTS 9,569,001 B2 *   2/2017  Mistry ................. H04N 9/3173
10,779,085 B1 *  9/2020  Carrigan ............. G06F 3/04812
(Continued)

FOREIGN PATENT DOCUMENTS

FR           2982681 A1      5/2013

OTHER PUBLICATIONS

English Machine Translation to Abstract of FR2982681.
(Continued)

*Primary Examiner* — David Phantana-angkool
(74) *Attorney, Agent, or Firm* — Cantor Colburn LLP

(57) ABSTRACT

A device for managing the effort for a gym hall adapted to broadcast a relative effort objective.
A system for piloting a gym hall including a sound broadcasting means, a visual broadcasting means, a lighting means, an effort management means, a human-machine interface, and a piloting means adapted to control, in an integrated manner and in real-time, the different means.
A support structure for such a system, comprising a substantially horizontal planar frame including peripheral beams and a central beam, adapted to support all components of the system.
A gym hall comprising a plurality of rectangular exercise stations, each station comprising a cardio apparatus, small exercise equipment, a rack and a central free space.

23 Claims, 2 Drawing Sheets

(51) Int. Cl.
    *A63B 24/00*         (2006.01)
    *G05B 19/042*      (2006.01)
    *G06F 3/14*          (2006.01)
    *G06F 3/16*          (2006.01)
    *H04H 20/61*       (2008.01)
    *H04R 29/00*       (2006.01)

(52) U.S. Cl.
    CPC ............ *G06F 3/1423* (2013.01); *G06F 3/165* (2013.01); *H04H 20/61* (2013.01); *A63B 2024/0068* (2013.01); *A63B 2071/065* (2013.01); *A63B 2071/0625* (2013.01); *A63B 2071/0658* (2013.01); *A63B 2071/0694* (2013.01); *G05B 2219/2664* (2013.01); *H04R 29/001* (2013.01)

(56) References Cited

U.S. PATENT DOCUMENTS

| | | | | |
|---|---|---|---|---|
| 2009/0128508 | A1* | 5/2009 | Sohn | G06F 3/0421 |
| | | | | 345/173 |
| 2010/0188340 | A1* | 7/2010 | Smoot | G06F 3/042 |
| | | | | 345/173 |
| 2015/0066526 | A1 | 3/2015 | Cheng et al. | |
| 2017/0357434 | A1* | 12/2017 | Coffman | G08C 17/02 |
| 2019/0026021 | A1* | 1/2019 | Coffman | G05B 15/02 |

OTHER PUBLICATIONS

International Search Report for Application No. PCT/FR2018/050426.

Written Opinion for Application No. PCT/FR2018/050426.

* cited by examiner

DEVICE FOR MANAGING EFFORT FOR A GYM HALL

CROSS REFERENCE TO RELATED APPLICATIONS

This application is a National Stage of PCT Application No. PCT/FR2018/050426 filed on Feb. 22, 2018, which claims priority to French Patent Application No. 17/51646 filed on Feb. 28, 2017, the contents each of which are incorporated herein by reference thereto.

TECHNICAL FIELD

The present invention concerns a «fitness» type gym hall.

BACKGROUND

The difficulty, for most people, to do physical exercise is due to the lack of motivation. The customers are waiting for a varied, renewed, playful and exciting experience. Sometimes neophyte, these customers are still waiting, in order to avoid mistakes, for an individual or at least customized guidance, by a coach.

BRIEF SUMMARY

Also the present invention proposes an innovative gym hall. This gym hall comprises a session piloting system using modern technologies to scientifically manage the efforts and to integrate different animation means, inspired by the show world and sound and light, in order to offer to the participant a new experience, combining effectiveness and performance, to a pleasant and motivating dimension. The piloting of the session is, under the control of a coach, managed almost automatically for all technical aspects by the piloting system, thus freeing the coach from secondary tasks to enable him to focus on the main role: the animation of the session, the accompaniment and the individualized follow-up of the participants.

The object of the invention is a device for managing the effort for a gym hall, comprising a broadcasting means adapted to broadcast in the gym hall, in real-time, an indicator corresponding to a relative effort objective, a relative effort preferably being split into a discrete number n of areas, each area being associated with a different indicator, with n preferably less than 10, and more preferably equal to 5.

According to other features of the effort management device:
  the indicators consist of colors, and the broadcasting means comprises at least one color projector adapted to color the gym hall with the color of the objective,
  the device further comprises: a measuring means adapted to measure an effort made by at least one participant, a relativization means, adapted to determine, starting from the measured achieved effort and personal data associated with the participant, an achieved relative effort and/or possibly in which area the achieved relative effort is located, and a broadcasting means adapted to broadcast in the gym hall, in real-time, an indicator corresponding to the achievement,
  the broadcasting means is comparative between said at least one participant.

The invention also concerns a system for piloting a gym hall comprising: a sound broadcasting means, a visual broadcasting means, a lighting means, an effort management means comprising such an effort management device, a human-machine interface, and a piloting means adapted to control, in an integrated manner and in real-time, the different means according to a session course, defined by a session synoptic preprogrammed and piloted by piloting commands.

According to other features of the session piloting system:
  the sound broadcasting means comprises a sound broadcasting list, at least one speaker, a means for managing the volume, and a monitoring means adapted to select a piece in said broadcasting list and to monitor the broadcast thereof on said at least one speaker, according to the session course,
  the sound broadcasting means further comprises a microphone, preferably wireless, and a mixing means adapted to mix the sounds originating from the microphone and the broadcasting list,
  the visual broadcasting means comprises a list of video sequences, at least one screen and a monitoring means adapted to select a video sequence and to monitor the broadcast thereof on said at least one screen and to display data, preferably originating from the effort management means, more preferably the achievement, on said at least one screen, according to the session course,
  the lighting means comprises at least one color projector adapted to color the gym hall with the color of the objective according to the session course,
  the human-machine interface is adapted to receive piloting commands among start, pause, resume, stop The invention also concerns a support structure for such a system comprising a substantially horizontal planar frame including peripheral beams and at least one central beam, adapted to be disposed at height relative to the gym hall and adapted to support all components of the system.

According to other features of the structure:
  the structure is adapted to support said at least one screen, comprising a first series of screens, disposed on either side and parallel to the central beam, and preferably dedicated to the broadcast of the video sequences,
  the structure is adapted to support said at least one screen, further comprising a second series of screens, disposed at the middle of the central beam, oriented at 45° with respect to the central beam, and preferably dedicated to the broadcast of the data,
  the structure also comprises at least two vertical posts supporting the frame,
  the structure is also adapted to support a human-machine interface, preferably hooked to a post or hanging under one of the beams,
  the beams and/or the posts are adapted to support said at least one color projector and said at least one speaker, said at least one color projector comprising at least one first color projector disposed and oriented so as to light the volume delimited under the frame, and at least one second color projector disposed and oriented so as to light the beams and/or posts,
  the beams and/or the posts are made with show-type rails,
  at least one beam or post is adapted to enable the hooking of a hanging strap, preferably the central beam.

The invention also concerns a gym hall comprising a plurality of rectangular exercise stations, organized in pairs disposed in parallel by the long side, the two stations of a pair facing each other by the short side, each station comprising a cardio apparatus disposed at the external end of the station, small exercise equipment, a rack disposed at the internal end of the station and adapted to enable the storage of said small equipment and a central free space between the cardio apparatus and the rack, each station preferably measuring 1.2×7 m, and the gym hall preferably comprising between 2 and 10 pairs of stations.

According to other features of the gym hall:
- the racks have a low profile, and two racks of a pair are assembled back to back and adapted to support the weight of a person,
- the gym hall also comprises such a session piloting system and such a support structure, with preferably the frame being substantially superimposed with the external limit of the stations, the possible posts resting on the external limit of the stations and the central beam being superimposed on the racks.

BRIEF DESCRIPTION OF THE DRAWINGS

The invention will be better understood on reading the following non-limiting description, with reference to the appended figures.

As illustrated in FIGS. 1-4, the invention concerns a gym hall 30. The organization of this gym hall 30 is based on an exercise station 31, substantially universal, and dedicated to a participant. Each exercise station 31 is designed to enable a participant to fully carry out a complete and varied session, comprising a variety of exercises alternating cardio workout and muscle relaxation/strengthening. For this purpose, and in order to optimize the use of the space, each exercise station 31 is rectangular, and paired with another similar station 31, the two stations 31 facing each other and being joined by the short side of the rectangle. The gym hall 30 comprises several ones of such pairs of stations disposed in parallel and joined by the long side. Each station 31 comprises a cardio apparatus 32, a set of small exercise equipment 33, a free space 34 and advantageously a rack 35, which may be disposed relatively in any manner whatsoever. According to a preferred embodiment, the cardio apparatus is preferably disposed at the external end (on the side adjacent to the external limit of the gym hall) of the station 31 and oriented so that the participant, in action on said cardio apparatus 32, looks towards the center of the gym hall 30. The cardio apparatus 32 is typically selected from a (fixed) bike, a rowing machine, a treadmill or any other equivalent equipment. A variety of cardio apparatuses 32 allows providing choices to the participant. The cardio apparatus 32 is typically the only variable element from one station 31 to another. Each cardio apparatus 32, irrespective of its type, allows carrying out, in a generic manner, all cardio exercises. The set of small exercise equipment 33 is advantageously identical from one station 31 to another so that each participant can perform all the exercises proposed with these small equipment 33. The small equipment 33 may include a «Hexa» type dumbbell set, a «kettle bell» dumbbell set, a «step» or «bench-step» stand, a «TRX» type hanging straps set, a floor mat or any other equivalent equipment. The rack 35 is preferably disposed at the internal end (on the side adjacent to the middle of the gym hall) of the station 31 and is adapted to enable the storage of said small equipment 33. The free space 34 is advantageously arranged in a central position between the cardio apparatus 32 and the rack 35. According to one embodiment, a rack is locked by means of a lock, for example electrical, in order to be monitored by the piloting system described later on. According to a preferred embodiment, each station 31 preferably measures 1.2×7 m. The base module is a pair of stations 31. It is thus possible, depending on the space available to install the gym hall 30, to modularly make a gym hall 30 with any number of base modules. Advantageously, a gym hall 30 comprises at least 2 such pairs, in order to be able to receive 4 participants and hope to create a team spirit and an emulation to practice together. In order to maintain a human dimension, and to enable the coach to effectively follow all participants during a session, a gym hall according to the invention comprises at most 10 of such pairs, in order to receive at most 20 participants. It should be noted that thanks to the technical assistance provided by the piloting system, the coach can actually supervise 20 participants in an effective manner.

Figure 1:
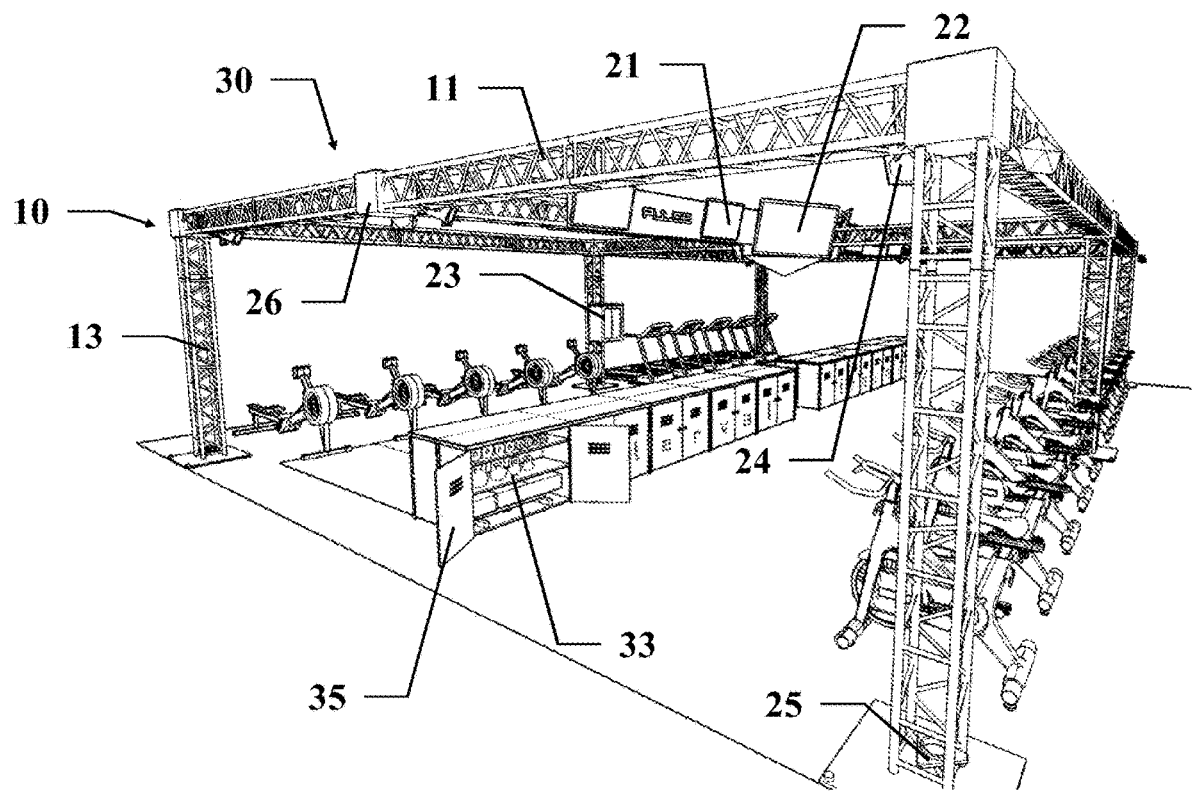
FIGS. 1 to 4 show in cavalier perspective, according to different viewpoints, a preferred embodiment of a gym hall according to the invention.

Such an organization of the exercise station 31 and of the gym hall 30, optimizes the use of space and thus financial profitability. A gym hall 30 according to the invention with 20 posts substantially occupies a surface area of 170 m$^2$ and offers a profitability comparable to a conventional gym hall of 800 m$^2$.

According to an advantageous feature, the racks 35, preferably identical, have a low profile, with a height of less than 1 m and preferably less than 50 cm, so as to maintain a visibility between the participants and particularly between the participants located on either side of the racks 35. In addition, two racks 35 of a pair are assembled back to back and advantageously adapted to support the weight of a person, so as to form a platform which may be used by the coach.

The invention also concerns a piloting system for a gym hall adapted to control in an integrated manner the different visual, sound and time components of a session. Such a piloting system comprises: a sound broadcasting means 26, a visual broadcasting means 21, 22, a lighting means 24, 25, a human-machine interface 23, and a piloting means adapted to control, in an integrated manner and in real-time, the different means 21, 22, 24, 25, 26. The piloting means is advantageously a computer system and this control is performed according to a session course. A session course comprises a preprogrammed session synoptic. A synoptic describes a substantially linear session in the form of a sequencing of blocks, possibly comprising sub-blocks, each corresponding to at least one exercise. Each exercise is at least defined by a type of exercise and a duration. It may be specified by other parameters such as the intensity of a relative effort. Each block or sub-block is advantageously associated with at least one sound broadcast, at least one visual broadcast, which may comprise at least one video sequence, at least one display of at least one image, at least one display of at least one datum, and/or else a lighting, where appropriate animated, etc. In order to keep control of the session, the synoptic is piloted during the session by means of piloting commands. These piloting commands are voluntarily reduced to two commands Start and Stop or else to four commands Start, Pause, Resume and Stop and are typically entered by the coach, using the human-machine interface 23. A session course is therefore a session synoptic, which defines the content, its sequencing, its duration, and the associated sound and visual means, piloted/conducted (start/stop) overtime.

The human-machine interface 23 is adapted to receive the piloting commands. The human-machine interface 23 comprises a physical device 23 enabling the coach to interact with the session piloting system. This device 23 may comprise any computer interface means such as a keyboard, a screen, a mouse or any other pointing device, or else advantageously a touchscreen/tablet. This device is advantageously grouped in a terminal 23 positioned so as to be easily accessible by the coach. This enables the coach to configure the session piloting system and to control the piloting means so as to manage the course of a session.

Thus, the piloting system assists by carrying out all automatable technical tasks (management of the sound effects: sounds, music, . . . , management of the visual effects: images, videos, lights, . . . ), leaving free hand to the coach on the advance, thus freeing him greatly in order to make him available to ensure the pedagogical accompaniment of the participants and the animation.

The sound broadcasting means comprises all the means for broadcasting an accompanying sound of an exercise and/or a session. Thus, it comprises a sound broadcasting list, comprising pre-recorded sound sequences, or means for producing/synthesizing them. This sound broadcasting list can comprise any sound, including music, such as: background music, music for supporting the exercises, special sound effect to support the show aspect, support and/or counting rhythm, time countdown, metronome, repetition counting, etc. This broadcasting list can advantageously be updated in order to add new sounds, such as new music, in order to stay up to date and broadcast the latest successful hits. It also comprises at least one speaker 26. It may also comprise any processing means: amplifier, equalizer, filter, special effects generator, etc. It also comprises a means for managing the volume. It also comprises a monitoring means adapted to select a piece in said broadcasting list and to monitor the broadcast thereof on said at least one speaker 26, according to the session course. The monitoring means advantageously selects a piece of the broadcasting list according to indications contained in the session synoptic. It advantageously monitors the broadcast in connection with the session course and the configuration parameters contained in the session synoptic. Thus, for example, a background music associated with an exercise block may continue to be broadcast, including when said block is in pause, while a countdown of the remaining time may on the contrary be paused when said block is in pause. A sound, including a music, is advantageously associated, by the synoptic, with an exercise, in rhythmic connection with the intensity of the exercise, in order to support the participants during the exercise.

According to another feature, another sound source is the voice of the coach, useful to enable him to animate the session and to intervene in a suitable and personalized manner with the participants. This voice replaces or superimposes with the previous sounds from the broadcasting list. For this purpose, the sound broadcasting means further comprises a microphone, preferably wireless and hands-free, carried by the coach and adapted to capture his voice, and a mixing means adapted to mix the sounds originating from the microphone and the broadcasting list. Advantageously, the mixing means comprises a function for automatically attenuating the other sounds, in order to favor the voice when the coach speaks in the microphone.

The visual broadcasting means comprises a list of video sequences, at least one screen 21, 22 and a monitoring means adapted to select a video sequence and to monitor the broadcast on said at least one screen 21, 22. In addition, the monitoring means is still adapted to display data, preferably originating from the effort management means, more preferably the achievement, on said at least one screen 21, 22, according to the session course.

The visual broadcast medium comprises all means for broadcasting accompanying images or videos of an exercise and/or a session. Thus, it comprises a list of video sequences comprising video sequences, including prerecorded fixed images. This list of video sequences may comprise any video, including fixed images, such as: background or entertainment videos, videos for supporting the exercises, such as instructional videos explaining and/or demonstrating the current exercise, but also special effects videos to support the show aspect, time countdown videos, repetition counting videos, etc. This broadcasting list can be advantageously updated to add new video sequences, such as new clips, in order to stay up to date by broadcasting the latest successful hits or provide a new tutorial for an exercise. The visual broadcasting means also comprises at least one screen 21, 22. It further comprises a monitoring means adapted to select a video sequence in said video sequence list and to monitor the broadcast thereof on said at least one screen 21, 22, according to the session course. The monitoring means advantageously selects a video sequence from the video sequence list according to indications contained in the session synoptic. It advantageously monitors the broadcast in connection with the session course and the configuration parameters contained in the session synoptic. Thus, for example, a background video associated with an exercise block may continue to be broadcast, including when said block is in pause, while a tutorial video can be paused when said block is in pause. A video is advantageously associated, by the synoptic, with an exercise, in thematic connection with the exercise: for example a tutorial.

The visual broadcasting means is also adapted to display data. This data can be of any type: list of participants, data relating to the exercise or to the session (name of the exercise, burned calories, involved muscle groups, remaining duration, total duration, next exercise), or also display of the results at the end of the session, etc. According to a preferred embodiment, these data comprise those originating from the effort management means, described later on.

The lighting means may comprise any type of lighting or lighting accessory: lights, stroboscope, mirror, laser, etc. The aim is to animate a session by possibly creating light effects in the manner of a concert or a sound and light show. According to a preferred feature, the lighting means comprises at least one color projector adapted to color the gym hall according to a number of different colors, for example 4 colors. This can be used in connection with the effort management means, as will be described later on.

According to an advantageous feature, the session piloting system comprises an effort management device. It is important, for a session to be profitable, to vary the effort intensities. It is also important to monitor, advantageously self-monitor by the participant himself, that at any time a level of effort intensity is optimal: neither too low nor too high. The representative parameter of the effort intensity is the heart rate. In order to personalize and adapt the effort to each one, the effort is relativized. Thus, a relative effort is expressed as a percentage, typically of a maximum heart rate, specific to each one and mainly depending on the age. Thus, a relative effort of 60% corresponds to a low effort intensity for everyone. This relative effort may correspond to a heart rate of 120 BPM for a 20-year-old participant, but to a heart rate of 90 BPM for a 70-year-old participant.

Also, according to an advantageous feature, the effort management device indicates, in real-time, in a manner accessible to the participant, a relative effort objective. For this purpose, the effort management device comprises a broadcasting means 24, 25 adapted to broadcast in the gym hall 30, in real-time, an indicator corresponding to a relative effort objective. Using a relative effort, allows giving a common objective to all participants while being interpreted by each one depending on his capacities and thus adapted to each one. The objective at a given moment is known from the piloting system by the session synoptic which indicates, at any time, a relative intensity, in connection with the current exercise/phase.

The indicators can be of any type. According to a preferred embodiment, using a visual modality, the indicators consist of colors. Also the broadcasting means comprises at least one color projector 24, 25, adapted to project a plurality of colors, in order to color the gym hall 30 with a color indicative of the objective.

According to an alternative or complementary feature, using a sound modality, the indicators may consist of sound tones, and/or rhythms, broadcast by means of said at least one speaker 26 and audibly perceived by the participants.

According to another advantageous feature, a relative effort is split into a discrete number n of areas. In other words, the total interval 0-100% of variation of the relative effort is divided into n areas making a partition: the intersection of any two areas is empty and the union of all areas is the total interval. The number n of areas is preferably less than 10, and more preferably equal to 5. Each area is associated with a different indicator, thus allowing limiting the number of indicators. According to an illustrative embodiment, the following five relative effort areas are defined: a first area corresponds to a relative effort/intensity of less than 60%, a second area corresponds to an intensity comprised between 60 and 70%, a third area corresponds to an intensity comprised between 70 and 80%, a fourth area corresponds to an intensity comprised between 80 and 90% and a fifth area corresponds to an intensity comprised between 90 and 100%. By using color indicators, it is possible to associate, in an illustrative manner, the following colors, offering a mnemonic gradation: the first area corresponds to a rest area and is not used in a session, also it has no need for an indicator/color, otherwise an absence of color, the second area is associated with the blue color, the third area is associated with the green color, the fourth area is associated with the yellow color and the fifth area is associated with the red color. Also a color projector, capable of producing these four colors may be used. Such color projectors, for example led projectors, are known.

Such a color lighting of the gym hall 30 according to the color of the objective area, in real-time, enables a participant to easily perceive the instruction at any time during the session. Indeed, the lighting is advantageously sufficiently diffuse so that the color is visible to a participant regardless of the direction in which he gazes.

In addition, in order to enable a participant to locate himself relative to the objective, the effort management device is also adapted to indicate to the participant his own or achieved relative effort level. For this purpose, the effort management device further comprises a measuring means adapted to measure the effort made by the participant, in real-time. This is typically achieved by an individual heart rate sensor, of a known type, advantageously wireless. Each participant carries such an individual sensor, for example in the form of a bracelet. The effort measured and transmitted to the system is then relativized by a relativization means. For this purpose, the relativization means has access to personal data associated with the participant, such as his maximum heart rate and/or his age. This allows determining, starting from the measured achieved effort and the personal data, an achieved relative effort. As for the objective, the achievement may be split into areas, advantageously using the same areas, in which case the relativization means can determine in which area the achieved relative effort is located. The device for managing the effort further comprises a broadcasting means adapted to broadcast in the gym hall 30, in real-time, an indicator corresponding to the achievement. This achievement is, according to the embodiment, the achieved relative effort made and/or the achieved area.

The personal data associated with the participant may also include other physiological data such as his size, weight, sex, morphology, level of practice and/or antecedents in order to refine the relativization calculation or offer him more suited exercises. They may also comprise his name, in order to display it opposite to his achievement or his results, as well as other data such as his e-mail in order to transmit to him his results or customized progress advices, and this as of the end of the session, etc.

According to a preferred embodiment, the achievement is displayed on a screen 21, 22. This display may be digital or preferably graphical and analog. Advantageously, this display is referenced relative to the objective so that the participant could locate his effort relative to the objective effort. Thus, according to one possible embodiment, the objective being indicated by a color indicator, the achievement is advantageously displayed by taking on the same color indicators, so that the participant could monitor, at a glance if he is or not in the objective. In order to constitute a reference, the achievement may advantageously be displayed beside, opposite and/or relative to the objective.

According to another feature, in order to improve the motivation of the participants, emulation is advantageously created by presenting the achievements of the participants in a comparative manner. Thus, it is possible to display side by side on the same broadcasting means 21, 22 the achievements of several participants, or even of all present participants, so that everyone could observe the achievements of the other participants and/or compare them to his achievement.

The different components of the session piloting system: speakers 26, screens 21, 22, lights 24, 25, terminal 23 of the human-machine interface, etc. are advantageously disposed at height. According to one embodiment, they may hang from the walls and/or ceiling of the building accommodating the gym hall 30. However, this requires an arrangement and may be impossible if the building is not suitable.

Also according to a preferred embodiment, a support structure 10 is dedicated to the support, the assembly and the integration of all components 21-26 of the piloting system. According to one embodiment, the structure 10 advantageously comprises a substantially horizontal planar frame 11. This frame 11 includes peripheral beams and at least one central beam 12. This frame is intended to be disposed at height, preferably at a height of 2.70 m, and to support all components 21-26 of the piloting system. This allows joining together all components 21-26 of the piloting system into an assembly structure 10 and to integrate them. This also allows creating a furniture which gives a pleasant aesthetic appearance to the gym hall 30. The support frame 11 may hang from the walls and/or ceiling of the building accommodating the gym hall 30, but with the same drawbacks as before.

The structure 10 is adapted to support the screen(s) 21, 22 of the visual broadcasting means. According to one embodiment, these screens 21, 22 comprise a first series of screens 21, disposed on either side and parallel to the central beam 12. These screens 21 of the first series are preferably dedicated to the broadcast of the video sequences. The arrangement on either side of the central beam 12 advantageously enables any participant to see at least one of these screens 21, which all advantageously broadcast the same video sequence.

Figure 2:
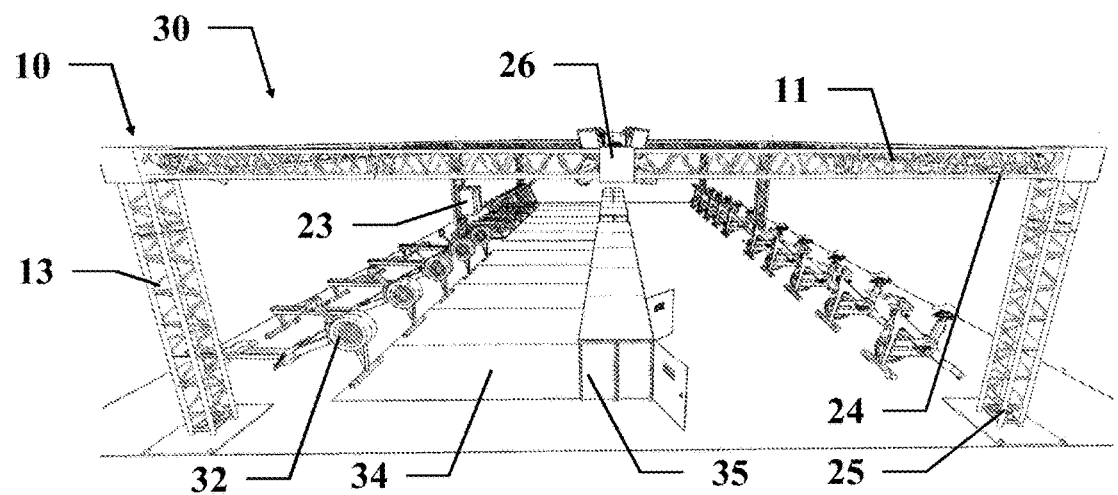
Figure 3:
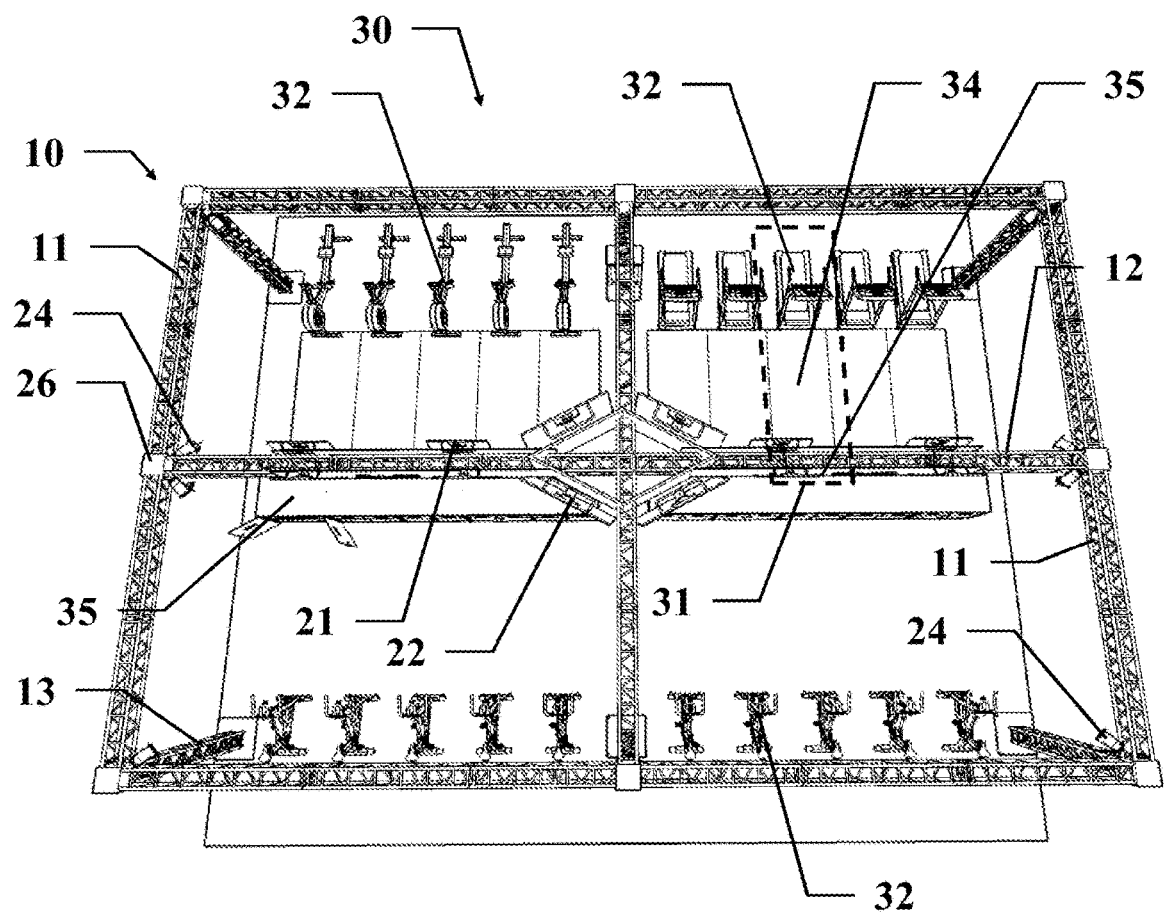
Figure 4:
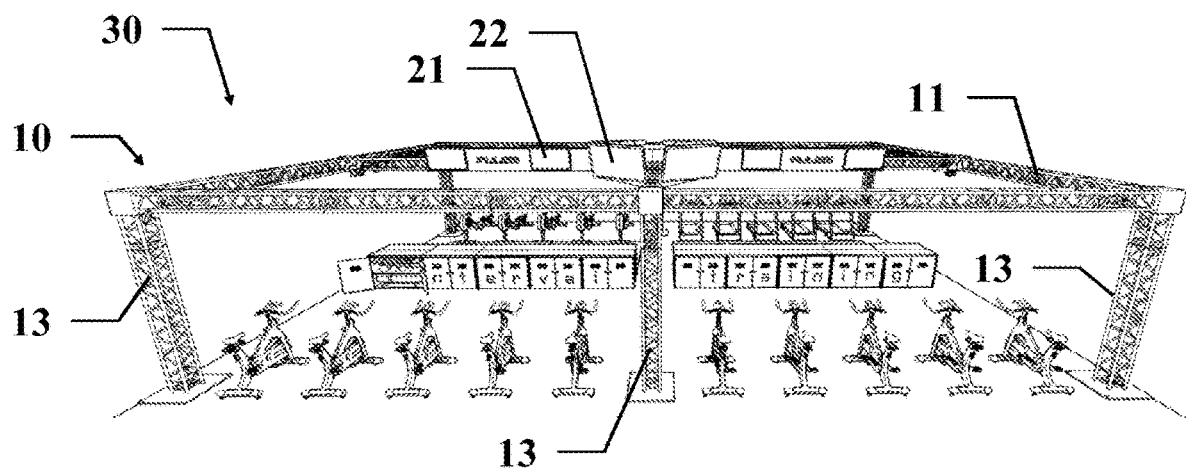

The size of the screens 21 of the first series is adapted to a vision from the bottom of the exercise station 31, the participant being on the cardio apparatus 32. There may be provided one screen 21 per station/participant, but this is not necessary. One screen 21 for several stations 31 is sufficient. In addition, a spacing of the screens 21 is advantageous in that it allows placing an advertising element, such as a logo, in the free spaces between two screens 21. As an indication, the screens 21 represented in FIGS. 1-4 have a width of 100 cm.

According to another embodiment, the screens 21, 22 of the visual broadcasting means further comprise, in an alternative or complementary manner, a second series of screens 22, disposed at the middle of the central beam, substantially oriented at 45° with respect to the central beam. These screens 22, at most 4 in number, are disposed in the diagonal of the corner of each corner/quarter of the hall and are substantially oriented at 90° with respect to each other. These screens 22 of the second series are preferably dedicated to the broadcast of data. The arrangement is advantageous in that it enables every participant to see at least one of these screens 22, which all advantageously broadcast the same views. Thus, according to one possible embodiment, these screens 22 display the data originating from the effort management device, and preferably the achievements of at least the participants of the quarter-gym hall being opposite to each other and preferably the achievements of all participants present in the gym hall 30. As an indication, the screens 22 represented in FIGS. 1-4 have a width of 165 cm.

In order to overcome the aforementioned drawback, of a building that is unadapted to support the components or the frame, according to one feature, the structure 10 further comprises at least two vertical posts 13 supporting the frame 11. Depending on the size of the hall/structure, two posts 13, advantageously diagonal may be sufficient. If the size or the weight of the frame 11 and its carriers requires so, four posts 13, at the four corners of the frame 11 are possible. A configuration with six (as illustrated in FIGS. 1-4) or eight posts 13 is still possible, the additional posts being disposed at the two or four middles of the branches of the frame 11. It is thus advantageously possible to avoid a central post that would unnecessarily clutter the hall and cut the view.

The posts 13 have many advantages. They allow making the structure 10 self-supporting, and thus independent of the building and even compatible with an installation without building: outdoors or under a marquee. They define the height where the frame 11 is located, which is typically 2.70 m. The posts 13 allow accommodating some of the components of the piloting system. The posts 13 reinforce the aesthetic appearance. Such an organization of the structure 10 may advantageously be dismountable in order to make it nomadic. These two self-supporting and dismountable features, open up the possibility for occasional, event uses.

A human-machine interface terminal 23, is also supported by the structure 10. It is preferably hooked to a post 13, as illustrated in FIGS. 1-4, for a peripheral arrangement. It may also be hanging under one of the beams 11, 12, for example under the middle of the central beam 12 for an arrangement at the center of the gym hall 30.

According to one feature, the beams 11, 12 and/or posts 13 are adapted to support said at least one color projector 24, 25 and said at least one speaker 26. Said at least one color projector 24, 25 comprise at least one first color projector 24 disposed and oriented to light the volume delimited under the frame and therefore the exercise stations 31 of the gym hall 30. Said at least one color projector 24, 25 further comprise at least one second color projector 25 disposed and oriented so as to light the beams 11, 12 and/or posts 13. The structure 10 is advantageously painted with a light and/or bright color, such as white, gray or metal in order to form a screen to the lights and have a nice aesthetic appearance. Thus, by means of the second color projectors 25, the structure 10 itself changes color to indicate the objective.

According to another feature, the beams 11, 12 and/or the posts 13 are made with show-type rails, as illustrated in FIGS. 1-4. This reuse advantageously allows using a material that is proven for such a construction. These rails are adapted to be assembled and have means for fastening and/or orienting the components that they support. In addition, this reuse advantageously recalls a concert/show context that we wish to replicate. Further advantageously, these show-type rails are hollow. This allows housing at least some of the components and wiring of the piloting system inside the section of the rail in order to improve the aesthetics. In addition, as illustrated more particularly in FIGS. 1-2, the second color projectors 25 may advantageously be installed inside the section of the rail. This allows making a coloration effect of the beams 11, 12 and/or posts 13 which comes from inside the structure 10.

Another function of the structure 10 is to provide at least one high point for hooking one hanging strap per station 31. At least one hanging strap may be included in the set of small equipment 33 and when an exercise uses it, each participant should be able to use a hooking point. The arrangement of the gym hall 30, in connection with the central beam 12 advantageously allows making such a high hooking point, for example at the level of the central beam 12.

According to a preferred embodiment, the gym hall 30 is organized with the periphery of the frame 11 being substantially superimposed with the external limit of the posts 31. If there are posts 13, the feet thereof rest on the external limit of the posts 31. In order to properly dispose the screens 21, 22 and serve as support to the hanging straps, the central beam 12 is advantageously superimposed with the middle double row of racks 35.

If the racks 35 are equipped with a lock monitored by the piloting system, the piloting system can advantageously unlock the racks 35 at the beginning of a session in order to allow access to small equipment 33 during the session and lock the racks 35 at the end of the session in order to prohibit access to small equipment 33.

The invention allows conducting a training session. Beforehand, a session synopsis is prepared. Such a synopsis comprises a succession of ordered exercises. The coach prepares this synopsis by selecting it from synopses provided by the distributor of the invention or by assembling predefined exercises/blocks provided by the distributor. Possibly, he can himself program an exercise/block. Each exercise is completed with all the necessary parameters concerning the sound, visual, lighting, intensity, etc. accompanying elements in order to enable the piloting system to conduct a session.

A typical session may be conducted in the following illustrative manner. After having chosen or built his synopsis, the coach loads it in the piloting system by means of a support such as a memory card, a USB key, or via a network. The coach welcomes the participants. The lighting is neutral. A connection of the effort sensors may be necessary and is performed for example via the human-machine interface 23. In addition, it may be necessary to carry out an operation to indicate to the piloting system which participants are present, in order to determine everyone's personal data. The coach invites each of the participants to take place at a station 31 thus by choosing his type of cardio apparatus 32. Once everyone is ready, the coach launches the session by a start command of the piloting system. The session synopsis is being conducted, one block after another, each one comprising one or several exercise(s). Throughout the entire session, the piloting system manages the sounds, including music, the displays on the screens, the lights, for example a color depending on the objective, and the coach intervenes with the voice. At any time, the coach can pause. An automatic pause may be provided between each block/exercise. A typical session starts with a warm-up block, followed by several exercise blocks alternating cardio and/or muscle strengthening/stretching. Then typically come a calm-down block and a final block. The final block typically comprises stretching and is a time used to communicate the results, possibly relayed on the screens. The coach comments and provides progress advises and encouragements.

Apart from coached sessions, the gym hall 30 can be operated in free practice. The cardio apparatuses 32 remain accessible. The small equipment 33 may be entirely or partly enclosed in the racks 35 kept locked. The piloting system may be used to create a sound and visual background, according to a dedicated program. The lighting is neutral: there is no objective. The effort management device can be disconnected or used individually by displaying the achievement. The screens 21, 22 broadcast tutorials and/or video clips.

The invention claimed is:

1. A device for managing effort provided by participants for a gym hall, the device comprising an objective indicator broadcasting means adapted to broadcast, in the gym hall, in real-time, an objective indicator corresponding to a relative effort objective, the relative effort objective specifying an exercise to be performed by the participants, a relative effort being split into a discrete number n of areas, each area being associated with a different objective indicator, n being less than 10, the device further comprising:
   an individual measuring means for measuring an achieved effort, achieved by one of the participants, in real-time,
   a relativization means, for determining, from the measured achieved effort and personal data associated with the one of the participants, an achieved relative effort and/or in which area the achieved relative effort is located, and
   an achieved relative effort broadcasting means for broadcasting in the gym hall, in real-time, an achieved relative effort indicator corresponding to the achieved relative effort and/or in which area the achieved relative effort is located.

2. The device according to claim 1, wherein the objective indicator is a color, and wherein the objective indicator broadcasting means comprises at least one color projector adapted to color the gym hall with the color of the relative effort objective, and wherein n is equal to 5.

3. The device according to claim 1, wherein the achieved relative effort broadcasting means is configured to compare the achieved relative efforts of at least two participants.

4. A system for piloting a gym hall, the system comprising:
   a sound broadcasting means,
   a visual broadcasting means,
   a lighting means,
   an effort management means, comprising a device according to claim 1,
   a human-machine interface, and
   a piloting means adapted to control in an integrated manner and in real-time the sound broadcasting means, the visual broadcasting means, the lighting means and the effort management means in function of a session course, defined by a session synoptic preprogrammed and piloted by piloting commands.

5. The system according to claim 4, wherein the sound broadcasting means comprises a sound broadcasting list, at least one speaker, a volume managing means for managing a volume, and a sound monitoring means adapted to select a piece in said broadcasting list and to monitor a sound broadcast thereof on said at least one speaker, in function of the session course.

6. The system according to claim 4, wherein the sound broadcasting means further comprises a microphone, and a sound mixing means adapted to mix sounds originating from the microphone and from a sound broadcasting list.

7. The system according to claim 4, wherein the visual broadcasting means comprises a list of video sequences, at least one screen and a video monitoring means adapted to select a video sequence and to monitor a video broadcast thereof on said at least one screen and to display data, originating from the effort management means, wherein the data includes the achieved relative effort and/or in which area the achieved relative effort is located, on the at least one screen, in function of the session course.

8. The system according to claim 4, wherein the lighting means comprises at least one color projector adapted to color the gym hall with the color of the relative effort objective in function of the session course.

9. The system according to claim 4, wherein the human-machine interface is adapted to receive a piloting command among start, pause, resume, stop.

10. A support structure for a system according to claim 4, the support structure comprising a substantially horizontal planar frame including peripheral beams and at least one central beam, the substantially horizontal planar frame being adapted to be arranged at a relative height in the gym hall and being adapted to support the system.

11. The support structure according to claim 10, being adapted to support at least one screen, the at least one screen comprising a first series of screens, disposed on both sides of the central beam and being parallel to the central beam, the first series of screens being dedicated to a video broadcast.

12. The support structure according to claim 10, being adapted to support at least one screen, the at least one screen further comprising a second series of screens, disposed at the middle of the central beam, oriented at 45° with respect to the central beam, and dedicated to a broadcast of the data.

13. The support structure according to claim 10, further comprising at least two vertical posts supporting the substantially horizontal planar frame.

14. The support structure according to claim 13, being adapted to support a human-machine interface, hooked to one of the at least two vertical post or hanged under one of the peripheral beams and the central beam.

15. The support structure according to claim 13, wherein the peripheral beams and/or the central beam and/or the at least two vertical posts are adapted to support at least one color projector and at least one speaker, the at least one color projector comprising at least one first color projector disposed and oriented so as to light a delimited area under the substantially horizontal planar frame, and at least one second color projector disposed and oriented so as to light the peripheral beams and/or the central beam and/or the at least two vertical posts.

16. The support structure according to claim 13, wherein the peripheral beams and/or the central beam and/or the at least two vertical posts are made with show-type rails.

17. The support structure according to claim 13, wherein at least one of the peripheral beams, central beam and the at least two vertical posts, the central beam, is adapted to enable a hooking of a hanging of a strap.

18. A gym hall comprising:
a plurality of rectangular exercise stations, organized in pairs disposed in parallel along a long side of the plurality of rectangular exercise stations, two stations of a pair of the plurality of rectangular exercise stations facing each other, each of the plurality of rectangular exercise stations comprising a cardio apparatus disposed at an external end of the plurality of rectangular exercise stations, small exercise equipment, a rack disposed at an internal end of the plurality of rectangular exercise stations and adapted to enable the storage of the small exercise equipment and a central free space between the cardio apparatus and the rack, each of the plurality of rectangular exercise stations measuring 1.2×7 m, and the gym hall comprising between 2 and 10 pairs of plurality rectangular exercise stations; and
a system for piloting a gym hall, the system comprising:
an effort management means, comprising a device for managing effort provided by participants of the gym hall, the device comprising an objective indicator broadcasting means adapted to broadcast, in the gym hall, in real-time, an objective indicator corresponding to a relative effort objective, the relative effort objective specifying an exercise to be performed by the participants, a relative effort being split into a discrete number n of areas, each area being associated with a different objective indicator, n being less than 10, the device further comprising:
an individual measuring means for measuring an achieved effort, achieved by one of the participants, in real-time,
a relativization means, for determining, from the measured achieved effort and personal data associated with the one of the participants, an achieved relative effort and/or in which area the achieved relative effort is located, and
an achieved relative effort broadcasting means for broadcasting in the gym hall, in real-time, an achieved relative effort indicator corresponding to the achieved relative effort and/or in which area the achieved relative effort is located.

19. The gym hall according to claim 18, wherein the rack has a short height, and two racks of the pair of the plurality of rectangular exercise stations are assembled back to back and adapted to support a weight of a person.

20. The gym hall according to claim 18, wherein the system comprises:
a sound broadcasting means,
a visual broadcasting means,
a lighting means,
a human-machine interface, and
a piloting means adapted to control in an integrated manner and in real-time the sound broadcasting means, the visual broadcasting means, the lighting means and the effort management means in function of a session course, defined by a session synoptic preprogrammed and piloted by piloting commands and a structure for the system, the support structure comprising a substantially horizontal planar frame including peripheral beams and at least one central beam, the substantially horizontal planar frame being adapted to be arranged at a relative height in the gym hall and being adapted to support the system, the substantially horizontal planar frame being substantially superimposed on an external limit of the rectangular exercise stations, at least two vertical posts resting on the external limit of the rectangular exercise stations and the central beam being superimposed on the rack.

21. The device of claim 1, wherein:
the measuring means includes an individual heart rate sensor for the participant, and
the personal data associated with the participant includes a maximum heart rate.

22. The device of claim 21, wherein the personal data associated with the participant further includes an age of the participant.

23. The device of claim 21, wherein the individual heart rate sensor is in a form of a bracelet.

* * * * *